(12) United States Patent
Jackson et al.

(10) Patent No.: US 11,647,762 B2
(45) Date of Patent: May 16, 2023

(54) METHOD AND COMPOSITIONS FOR REDUCING IMMUNORECOGNITION OF DIETARY PROTEIN

(71) Applicant: Hill's Pet Nutrition, Inc., Topeka, KS (US)

(72) Inventors: Matthew Jackson, Topeka, KS (US); Yanrong Liu, Lawrence, KS (US); Dennis Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 512 days.

(21) Appl. No.: 15/539,915

(22) PCT Filed: Dec. 27, 2014

(86) PCT No.: PCT/US2014/072457
§ 371 (c)(1),
(2) Date: Jun. 26, 2017

(87) PCT Pub. No.: WO2016/105442
PCT Pub. Date: Jun. 30, 2016

(65) Prior Publication Data
US 2018/0000102 A1  Jan. 4, 2018

(51) Int. Cl.
*A23C 9/127* (2006.01)
*G01N 33/68* (2006.01)
(Continued)

(52) U.S. Cl.
CPC ............ *A23C 9/1275* (2013.01); *A21D 8/042* (2013.01); *A23C 9/1216* (2013.01); *A23C 13/16* (2013.01);
(Continued)

(58) Field of Classification Search
CPC ......... A23C 9/1275; A23L 11/37; A23L 11/33
See application file for complete search history.

(56) References Cited

U.S. PATENT DOCUMENTS

| | | |
|---|---|---|
| 5,156,956 A | 10/1992 | Motoki et al. |
| 5,252,469 A | 10/1993 | Andou et al. |

(Continued)

FOREIGN PATENT DOCUMENTS

| | | |
|---|---|---|
| EP | 0610649 | 8/1994 |
| JP | 292706 B2 | 5/1999 |

(Continued)

OTHER PUBLICATIONS

Haza et al., "Use of a Monoclonal Antibody and Two-Enzyme-Linked Immunosorbent Assay Formats for Detection and Quantification of the Substitution of Caprine Milk for Ovine Milk", Journal of Food Protection, vol. 60, No. 8, 1997, pp. 973-977. (Year: 1997).*

(Continued)

*Primary Examiner* — Stephanie A Cox (57) ABSTRACT

The present disclosure is directed to a method for reducing immunoreactivity of a food including (a) incubating a food that contains at least one protein with a cross-linking enzyme to form a food that includes at least one cross-linked protein; and (b) fermenting the food including the at least one cross-linked protein with a microorganism to form a modified food including a hydrolysate of the at least one cross-linked protein, wherein (a) is performed before (b) and wherein a level of immunoreactivity of the modified food is less than a level of immunoreactivity of an unmodified food including at least one protein. Modified foods obtained from the present method are also provided.

18 Claims, 2 Drawing Sheets

(51) Int. Cl.
| | |
|---|---|
| A23C 9/12 | (2006.01) |
| A23J 3/34 | (2006.01) |
| A23L 11/30 | (2016.01) |
| A23L 5/20 | (2016.01) |
| A21D 8/04 | (2006.01) |
| A23C 21/02 | (2006.01) |
| A23C 17/02 | (2006.01) |
| A23C 13/16 | (2006.01) |
| A23L 25/00 | (2016.01) |

(52) U.S. Cl.
CPC .............. *A23C 17/02* (2013.01); *A23C 21/02* (2013.01); *A23J 3/34* (2013.01); *A23L 5/25* (2016.08); *A23L 5/28* (2016.08); *A23L 11/33* (2016.08); *A23L 11/37* (2016.08); *A23L 25/00* (2016.08); *G01N 33/6893* (2013.01); *A23V 2002/00* (2013.01); *A23Y 2220/67* (2013.01); *A23Y 2260/35* (2013.01); *A23Y 2280/15* (2013.01); *G01N 2333/91085* (2013.01); *G01N 2800/24* (2013.01)

(56) References Cited

U.S. PATENT DOCUMENTS

| | | | | |
|---|---|---|---|---|
| 2010/0266724 | A1* | 10/2010 | Tams | A23C 9/1213 426/42 |
| 2011/0129568 | A1* | 6/2011 | Fukui | A23C 9/123 426/43 |

FOREIGN PATENT DOCUMENTS

| | | |
|---|---|---|
| WO | 2007/060288 | 5/2007 |
| WO | 2010/103126 | 9/2010 |
| WO | WO 2014/007665 | 1/2014 |

OTHER PUBLICATIONS

Lorenzen et al., 2002, "Effect of enzymatic cross-linking of milk proteins on functional properties of set-style yoghurt," International Journal of Dairy Technology 55(3):152-157.

Ozer et al., 2006, "Incorporation of microbial transglutaminase into non-fat yogurt production," International Dairy Journal 17(3):199-207.

De Angelis et al., 2006, "VSL#3 probiotic preparation has the capacity to hydrolyze gliadin polypeptides responsible for Celiac Sprue," Biochim Biophys Acta 1762:80-93.

De Angelis et al., 2010, "Mechanism of degradation of immunogenic gluten epitopes from *Triticum turgidurn* L. var. *darum* by Sourdough Lactobacilli and fungal proteases," Appl. Environ. Microbiol. 76(2):508-518.

Frias et al., 2008, "Immunoreactivity and amino acid content of fermented soybean products," Journal of Agricultural and Food Chemistry 56(1):99-105.

International Search Report and Written Opinion in International Application No. PCT/US2014/072457, dated Sep. 5, 2015.

Klein et al. 1992, "Purification and partial characterization of transglutaminase from Physarum polycephalum," Journal of Bacteriology 174(8):2599-2605.

Leszczynska et al., 2006, "The use of transglutaminase in the reduction of immunoreactivity of wheat flour," Food and Agricultural Immunology 17(1-4):105-113.

Olivier et al. 2012, "Allergenicity of Bos d 5 in Children, with Cow's Milk Allergy is Reduced by Transelutaminase Polymerization," Pediatric Allergy, Immunology, and Pulmonology 25:30-33.

Olivier et al. 2012, "In search of a tolerance-induction strategy for cow's milk allergies: significant reduction of beta-lactoglobulin allergenicity via transglutaminase/cysteine polymerization," Clinics (Sao Paul), 67(10):1171-1179.

Phromraksa et al., 2008, "Identification of proteolytic bacteria from Thai traditional fermented foods and their allergenic reducing potentials," J. Food Science 73(4):M189-195.

Rahman et al., 2012, "Characterization of seafood proteins causing allergic diseases," in Allergic Diseases-Highlights in the Clinic, Mechanisms and Treatment, C. Pereira (Ed), IBSN:978-953-51-0227-4, InTech.

Rizzello et al., 2014, "Use of fungal proteases and selected sourdough lactic acid bacteria for making wheat bread with an intermediate content of gluten," Food Microbiology 37:59-68.

Van Esch et al., 2013, "Sensitizing capacity and allergenicity of enzymatically cross-linked sodium caseinate in comparison to sodium caseinate in a mouse model for cow's milk allergy," Toxicology Letters 218:50-55.

Villas-Boas et al., 2010, "The effect of transglutaminase-induced polymerization in the presence of cysteine on beta-lactoglobulin antigenicity," International Dairy Journal 20:386-392.

Wroblewska et al., 2009, "Influence of the addition of transglutaminase on the immunoreactivity of milk proteins and sensory quality of kefir," Food Hydrocolloids 23(8):2434-2445.

Wroblewska et al., 2010, "Impact of transglutaminase reaction on the immunoreactive and sensory quality of yoghurt starter," World Journal of Microbiology and Biotechnology 27(2):215-227.

Wroblewska et al., 2011, "Immunoreactivity of transglutaminase cross-linked milk proteins in fermented milk product obtained with Lactobacillus acidophilus," Post. Dermatol. Alergol., XXVIII, 4:261-267.

Wroblewska et al., 2013, International Journal of Food Science and Technology 48(5):1007-1017.

Zhou et al., 2013, "Peanut allergy, allergen composition, and methods of reducing allergenicity: A Review," International Journal of Food Science 2(2):3-8.

* cited by examiner

METHOD AND COMPOSITIONS FOR REDUCING IMMUNORECOGNITION OF DIETARY PROTEIN

BACKGROUND

A food allergy is defined as an abnormal immunological reaction to food proteins, which causes an adverse clinical reaction. In the United States, as of 2008, 6-8% of children and 4% of adults are affected with a food allergy. Pets, such as dogs and cats, are also affected by food allergies. The incidence of food allergy has been increasing over the years, and to date, no effective treatment of food allergies is available. Therapies involving drugs (antihistamines, decongestants, or steroids) only combat the symptoms of an allergic reaction and do not prevent allergenic reactions due to future exposure to the allergen.

It has been reported that the best way to prevent unintended exposure to a food allergen is the strict avoidance of foodstuffs containing allergens. However, such avoidance may not always be possible. Furthermore, complete elimination of foodstuffs causing allergy may have a negative impact on a healthy diet as about 90% of allergens are present in food of high nutritional value (e.g., milk, eggs, fish, shellfish, tree nuts, peanuts, wheat, and soybeans). Therefore production of hypoallergenic food for both humans and companion animals is desirable.

There are an increasing number of publications describing attempts to reduce allergenicity. However, to date, such attempts have had variable success. For example, it has been reported that introducing cross links into milk proteins with transglutaminase during fermentation reduces the immunoreactivity of some milk protein allergens, but increases the immunoreactivity of a major milk allergen, β-casein. Accordingly, there remains a strong desire in the art to provide new techniques and methods that are more effective in reducing allergenicity than the presently available techniques.

BRIEF SUMMARY

The present disclosure is directed to techniques, systems, and methods for reducing immunoreactivity of a food including (a) incubating a food that contains at least one protein with a cross-linking enzyme to form a food that includes at least one cross-linked protein; and (b) fermenting the food including the at least one cross-linked protein with a microorganism to form a modified food including a hydrolysate of the at least one cross-linked protein, wherein (a) is performed before (b) and wherein a level of immunoreactivity of the modified food is less than a level of immunoreactivity of an unmodified food including at least one protein.

Also provided herein is a modified food including: a hydrolysate including: a cross linked protein, wherein the protein is selected from the group consisting of: α-casein, β-casein, β-lactoglobulin, α-lactoglobulin, gliadin, ovalbumin, Gly m Bd 30K, iso Ara h3, parvalbumin, tropomyosin and arginine kinase (40 kDa), wherein at least 10% of polypeptides in the hydrolysate range from 1,000 daltons to 5,000 daltons and wherein at least 10% of the polypeptides in the hydrolysate range from about 50,000 daltons and 500,000 daltons, and wherein a level of immunoreactivity of the modified food is less than a level of immunoreactivity of an unmodified food.

Further areas of applicability of the present disclosure will become apparent from the detailed description provided hereinafter. It should be understood that the detailed description and specific examples, while indicating embodiments of the disclosure, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIG. 1 shows a decrease of immunoreactivity of purified milk-derived β-casein after incubation with transglutaminase.

FIG. 2 shows a transglutaminase dose dependent reduction in ELISA immunoreactivity of purified β-casein.

FIG. 3 shows that transglutaminase effectively reduces immunoreactivity of β-casein in a milk matrix.

FIG. 4 shows that a combination of transglutaminase and microbial fermentation reduces immunoreactivity of β-casein in a milk matrix to a greater extent than the sum of the individual effects of these processes, as described in the Example.

DETAILED DESCRIPTION

The following description of the embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In some embodiments, the present disclosure is directed to methods for forming foods having reduced immunoreactivity, i.e., the foods modified according to the present methods have a reduced capacity to bind to antibodies. Accordingly, the modified foods are less likely to evoke food allergies in sensitive individuals or animals. As is recognized in the art, a food allergy is an abnormal response of the immune system. Food allergies are caused by specific components in a food, usually the naturally occurring proteins, which are nontoxic and show no adverse effects in most individuals. However, when a sensitive individual or animal ingests an allergenic food, the allergen protein in the food is recognized by the immune system as an antigen, and an allergic reaction is induced. When T cells are stimulated by the antigen, they release the substances IL-4, IL-5, and IL-13 to activate and convert B cells into plasma cells that can secrete IgE, a class of antibody. IgE with specificity to the particular allergen will bind to the receptors of the mast cells and basophils so that they are activated to be sensitive cells. When the allergen is ingested into the body again, the allergen will be recognized as the antigen and bind to IgE on the surface of the mast cells and basophils, resulting in the degranulation of particles and the release of vesicles containing sensitizing factors, such as histamine. These sensitizing factors are then released into the blood and interact with the receptors on cells and tissues, thereby causing the symptoms of an allergic reaction. The allergic symptoms caused by food allergy and their severity depend on the individual physical conditions and the intake amount of the food allergen.

In some embodiments, the present methods may be used to modify the particular regions of proteins in foods, which induce food allergies, i.e. epitopes. An "epitope" as used herein is the portion of a molecule that is bound by an antibody. Accordingly, the techniques and methods of the present disclosure may be used to reduce the potential for a protein in a food to cause an allergic reaction in a sensitive individual or animal.

In some embodiments, the present disclosure is directed to modifying foods. In some embodiments, a "food" may encompass solely a protein. In other embodiments, the food may be a protein in a matrix. A "matrix" as used herein refers to additional fats, carbohydrates, fiber, vitamins and/or minerals and the like that are combined with the protein. In some embodiments, the food is a nutritionally complete food. In other embodiments, the food is a nutritionally incomplete food.

A "nutritionally-complete", "nutritionally-balanced" or "complete and nutritionally-balanced food" is one that contains all known required nutrients for the intended recipient or consumer of the food, in appropriate amounts and proportions based, for example, on recommendations of recognized or competent authorities in the field of animal (including human) nutrition. Such foods are therefore capable of serving as a sole source of dietary intake to maintain life without the addition of supplemental nutritional sources.

In some embodiments, the food is nutritionally incomplete. In these embodiments, while the food may contribute to the nutritional and caloric content of an animal's diet, the composition is not an independent source of an animal's complete daily nutritional and calorific needs.

The term "animal" as used herein refers to any animal including fish, birds, reptiles, and mammals such as dogs, cats, horses, pigs, cows, monkeys and humans, etc.

The foods, which may be modified according to the present methods include those foods that comprise at least one protein. The term "protein" as used herein refers to biological molecules, or macromolecules, consisting of one or more long chains of amino acid residues. The term protein also encompasses polypeptides, i.e. a linear chain of amino acid residues. Short polypeptides containing less than about 20-30 amino acid residues, that is, peptides, are also encompassed by this term.

Exemplary foods, which may be modified according to the present disclosure include but are not limited to: milk, meat, eggs, fishes, crustacean, mollusks, cereals, legumes and tree nuts. For example, milk includes raw and/or processed milk, whole or low fat milk including milk containing 1% or 2% milk fat, skim milk, buttermilk, reconstituted milk powder, condensed milk, dried milk, whey, whey protein concentrate, or cream. The milk may originate from any mammal, e.g., non-human primates, such as monkeys and chimpanzees, a human primate or farm animals such as cows, goats, sheep, swine, horses and cattle.

The term "meat" is understood to apply not only to the flesh of cattle, swine, sheep and goats, but to any species including but not limited to horses, whales and other mammals, poultry and fish. For example, the term "meat" encompasses flesh of mammalian species such as beef, veal, pork, horsemeat, bison, cows, deer, elk, lamb, and the like. The term "meat" further includes poultry meat such as chicken, turkey, duck, or goose and the like. Meat also includes striated muscle which is skeletal or that which is found, for example, in the tongue, diaphragm, heart, or smooth muscle such as found in the esophagus or stomach, with or without accompanying overlying fat and portions of the skin, sinew, nerve and blood vessels which normally accompany the meat flesh. The term "meat" further includes products such as organs and tissues including lungs, spleens, kidneys, brain, liver, blood, bone, partially defatted low-temperature fatty tissues, intestines free of their contents, and the like. Meat further includes non rendered clean parts of carcasses of slaughtered poultry such as heads, feet, and viscera, free from fecal content and foreign matter.

Additional foods, which may be used with the methods of the invention, include but are not limited to egg whites and egg yolks, mackerel, sardine, tuna, salmon, codfish, flatfish and salmon caviar of the fishes, crab, shrimp, blue mussel, squid, octopus, lobster, wheat, rice, buckwheat, rye, barley, oat, corn, millet, soybean, peanut, cacao, pea, kidney bean, hazelnut, Brazil nut, walnuts and almonds.

In some embodiments, the foods that may be modified according to the present disclosure include any food comprising at least one of the ingredients discussed above or combinations thereof.

Examples of suitable proteins that may be included in the food modified according to the present methods include but are not limited to β-lactoglobulin, α-lactoglobulin, *bovine serum albumin*, casein including α-casein, β-casein and κ-casein found in milk, ovalbumin found in eggs, myosin and actinomysin found in meat, gluten or gliadin found in wheat, Ara h 1, Ara h 2, and Ara h 3 found in peanut, Gly m Bd 30K found in soy, parvalbumin, a major clinical cross-reactive allergen found in fish, tropomyosin, a major allergen found in shellfish, crustaceans and mollusks and arginine kinase (40 kDa), an allergen found in shrimp. Other examples of seafood allergens may be found in Rahman et al. (2012), "Characterization of Seafood Proteins Causing Allergic Diseases", in *Allergic Diseases-Highlights in the Clinic, Mechanisms and Treatment*, Prof. Celso-Pereira (ed.), ISBN: 978-953-51-0227-4, InTech, which is herein incorporated by reference in its entirety. In some embodiments, foods containing casein, such as β-casein are used.

Cross-Linking

In some embodiments a food comprising at least one protein is first incubated with a cross-linking enzyme to form a food comprising at least one cross-linked protein. As used herein the terms "cross-link" "cross-linking" or "cross-linked" in reference to proteins means to introduce covalent bonds between and/or within proteins or peptides. Accordingly, a cross-linked protein is one into which covalent bonds have been newly introduced via enzymatic crosslinking, for example, within a protein native to the food and/or between the native protein and other native proteins, peptides or amino acids in the food composition. In some embodiments, a cross-linked protein has an increased molecular weight, a different 3 dimensional structure and/or a different charge in comparison to that of a native protein. Further, in some embodiments, cross-linking alters or destroys epitopes in the native protein rendering the epitopes unavailable to antibodies. In yet other embodiments, the cross-linking conceals one or more epitopes within the protein, rendering the epitopes unavailable to antibodies.

Enzymes that may be used to cross-link proteins include, but are not limited to, peroxidases, tyrosinases, laccases and transglutaminases. Peroxidases (PODs) are hem-containing enzymes, which catalyze the oxidation of a variety of organic compounds by hydrogen peroxide or hydroperoxides. Acting on phenolic compounds PODs generate o-quinones, which further react with other phenolics, amino, or sulfhydryl compounds in proteins to form cross-linked products. Protein disulfide isomerases and thioredoxins, which catalyze thiol-disulfide exchange leading to rearrangement of disulfides on proteins and potentially masking epitopes by steric hindrance of the epitope-antibody interaction are also contemplated.

In some embodiments, tyrosinases are used with the methods of the present disclosure. Tyrosinases are bi-functional enzymes catalyzing o-hydroxylation of monophenols (including protein-bound tyrosine residues) to o-diphenols and subsequent oxidation of o-diphenols to o-quinones. Reactive o-quinones can further undergo non-enzymatic polymerization or can react with amino acid residues in proteins. Tyrosinase (EC 1.14.18.1) from mushroom *Agaricus bisporus* and tyrosinase from filamentous fungi *Trichoderma reesei*, have been used as crosslinking tools in food processing. These tyrosinases act on proteins and peptides by catalyzing oxidation of tyrosine, resulting in oxidative cross-linking of tyrosine side-chains.

In some embodiments, cross-linking enzymes used with the present methods are laccases. Laccases catalyze oxidation of various phenolic compounds and may generate free radical species. Reactive free radicals can further undergo non-enzymatic polymerization or can react with high redox potential substrate targets, such as amino acid residues in proteins.

More typically, transglutaminases are used with the embodiments of the present disclosure. As used herein "transglutaminases", classified as EC 2.3.2.13, refer to enzymes capable of catalyzing acyl transfer reactions and introducing covalent crosslinks in proteins. In some embodiments, ε-amino groups of lysine residues and γ-carboxamide groups of glutamine residues in proteins act as acyl receptors and acyl donors, respectively. This reaction results in covalent isopeptide binding, which results in changes in molecular size of the protein.

The glutamine and lysine residues will often be present within the same protein molecule, but it is also possible to use the present process for coupling two different proteins, in which only one contains available glutamine residues and/or only one contains available lysine residues, or similarly, with three or even more different proteins. Such mixed crosslinking results in heteropolymers, which are also encompassed by the present disclosure.

An exemplary reaction catalyzed by a transglutaminase is shown below.

Transglutaminases that may be used with embodiments of the present disclosure may be of human, animal (e.g., bovine) or microbial origin. Examples of such transglutaminases are animal derived FXIIIa; microbial transglutaminases derived from *Physarum polycephalum* (see Klein et al., *Journal of Bacteriology*, 1992, Vol. 174, p. 2599-2605, which is herein incorporated by reference in its entirety), transglutaminases derived from *Streptomyces* species including *Streptomyces lavendulae* and *Streptomyces lydicus*. Other examples include transgluaminases obtained from *Streptoverticillum* species including *Streptoverticillium mobaraense*, *Streptoverticillium cinnamoneum*, and *Streptoverticillium griseocarneum* (see for example, U.S. Pat. No. 5,156,956 to Motoki et al. and U.S. Pat. No. 5,252,469 to Andou et al., which are each incorporated by reference in their entireties). Transglutaminases are also commercially available and may be obtained, for example, from the Ajinomoto Company in Japan, e.g., Activa®EB and Activa®WM, Sigma-Aldrich, St. Louis, Mo. and modernist Pantry, e.g., MooGloo® TI.

The amount of cross-linking enzyme, such as transglutaminase used in the method of the present disclosure is not particularly limited. In some embodiments, between 0.01 U and 15 U, more typically about 0.1 U to about 10 U or even more typically about 0.01 to about 2 units of cross-linking enzyme per gram of a food material may be used. The optimum amount of cross-linking enzyme varies depending on the type, size and form of the food material. The appropriate amount of cross-linking enzyme can be determined by routine experiments based upon the above-mentioned ranges. The combination of food and cross-linking enzyme are allowed to react for a period of about 0.5 hours to about 48 hours at about 2° C. to about 80° C., for example, or about 20 to about 40 hours at about 2° C. to about 5° C., more typically about 24 hours at about 4° C. In some embodiments, the degree of cross-linking of the protein in the food may be such that between about 0.1 to about 2 cross-links, such as about 0.5 to 1 cross-links, per native protein molecule are formed.

In some embodiments, after enzymatic cross-linking, the cross-linking enzyme is inactivated. This can be done by heating the food, now comprising the cross-linked protein molecules, with the cross-linking enzyme to a given temperature for a certain amount of time, where the temperature and the time are sufficient to inactivate the cross-linking enzyme. For example, cross-linking enzymes may be inactivated by heating for at least 3 minutes at 90° C. or higher Microbial Fermentation In some embodiments, the food comprising the at least one cross-linked protein is subsequently subjected to microbial fermentation. As used herein, "microbial fermentation" refers to the action of microorganisms on food, such that desirable biochemical changes cause modification to the food. In some embodiments, the desirable biochemical changes include the ability of microbial proteolytic enzymes to hydrolyze the at least one cross-linked protein in a food. As used herein, the phrase "hydrolyze" in regard to proteins or cross-linked proteins refers to the chemical reaction of a protein with water to produce two or more smaller molecules, e.g., polypeptides.

Without being bound by theory, it is believed that the microbial enzymes digest portions of the cross-linked protein in the food formed after incubation with cross-linking enzymes, and, accordingly, alter the structure of and/or destroy any epitopes that may remain intact or available to an antibody. Consequently, the altered or destroyed epitopes after microbial fermentation further reduce the immunoreactivity of a food containing the cross-linked protein.

It is further believed that bonds formed by cross-linking proteins may exhibit high resistance to proteolytic degradation (proteolysis). Accordingly, in some embodiments only a small portion of the cross-linked proteins may be hydrolyzed by microbial fermentation. Consequently, only a portion of the cross-linked proteins may be hydrolyzed by microbial fermentation are cleaved, resulting in a bi-modal molar mass distribution of the resulting polypeptides. The term "molar mass distribution" when used in reference to a hydrolyzed, cross-linked protein pertains to the molar mass of each polypeptide present in the cross-linked protein hydrolysate. For example, a cross-linked protein hydrolysate having a molar mass distribution of greater than 100,000 daltons means that each polypeptide included in the protein hydrolysate has a molar mass of at least about 10,000 daltons.

In some embodiments, the modified food product subsequent to microbial fermentation results in a hydrolysate of at least one cross-linked protein having two molar mass distributions. In certain embodiments, microbial fermentation of a food product comprising a cross-linked protein results in a hydrolysate in which at least about 5% to about 40%, more typically at least about 5% to about 25%, yet more typically at least about 10% to about 15% of the polypeptides have a molecular weight between about 500 daltons to about 10,000 daltons, more typically about 3,000 to about 8,000 daltons, even more typically about 3,000 daltons to about 5,000 daltons and yet even more typically from about 1,000 to 5,000 daltons.

In some embodiments, microbial fermentation of a food product comprising a cross-linked protein results in a hydrolysate in which about 5% to about 95%, more typically about 75% to about 95%, yet more typically about 80% to about 90% of the polypeptides have a molecular weight between about 50,000 daltons to about 500,000 daltons, more typically about 50,000 daltons to 150,000, such as 80,000 daltons to about 150,000 daltons and even more typically about 100,000 daltons to about 150,000 daltons.

In some embodiments, the food comprising at least one cross-linked protein is subjected to microbial fermentation for a time period of about two hours to about four days. More typically, the food comprising at least one cross-linked protein is subjected to microbial fermentation for a time period of about two days. In some embodiments, the food comprising at least one cross-linked protein is subjected to microbial fermentation for a time period of about one day.

In various embodiments, the temperature of the microbial fermentation is between about 20° C. to about 48° C. More typically, the temperature is about 20° C. to about 40° C. More typically, the temperature ranges from about 20° C. to about 22° C. In other embodiments, the temperature during fermentation ranges from about 37° C. to about 40° C.

In some embodiments, the microorganism used during microbial fermentation is a bacterium, a fungus or a combination thereof. For example, bacteria from the genera *Bacillus, Lactobacillus, Leuconostoc, Pediococcus, Streptococcus, Staphylococcus, Micrococcus* or a combination thereof may be used. In some embodiments, the *Bacillus subtilis, Bacillus licheniformis* or *Bacillus megaterium* or combinations thereof.

In some embodiments, the *Lactobacillus* is *Lactobacillus alimentarius, Lactobacillus brevis, Lactobacillus sanfranciscensis, Lactobacillus hilgardii, Lactobacillus helveticus, Lactobacillus fermentum, Lactobacillus lactis, Lactobacillus casei, Lactobacillus bulgaricus, Lactobacillus acidophilus, Lactobacillus plantarum* or combinations thereof.

In some embodiments, the *Leuconostoc* is *Leuconostoc mesenteroides*. In some embodiments, the *Pediococcus* is *Pediococcus acidilactici*. In some embodiments, the microorganisms used during fermentation are a combination of *Leuconostoc mesenteroides, Lactobacillus plantarum* and *Pediococcus acidilactici*.

In some embodiments, the *Streptococcus* is *Streptococcus diacetylactis, Streptococcus lactis* or a combination thereof. In some embodiments, the *Staphylococcus* is *Staphylococcus epidermis*.

In some embodiments, the microorganism is a fungus, such as a *Saccharomyces*, such as *Saccharomyces diastaticus* or *Saccharomyces cerevisiae*, an *Aspergillus*, such as, *Aspergillus oryzae*, a *Rhizopus*, e.g., *Rhizopus oryzae* or a *Mucor*, e.g., *Mucor miehei*. Any combination of the above-described exemplary bacterial or fungal strains may be used with the microbial fermentation of the present disclosure.

In some embodiments, about $10^3$ to $10^6$ fungal spores, more typically about $10^5$ fungal spores per gram of food comprising at least one cross-linked protein are used during microbial fermentation. In some embodiments, about $10^3$ to $10^6$ Colony Forming Units (CFU) of bacteria, more typically about $10^5$ CFU of bacteria per gram of food comprising at least one cross-linked protein are used during microbial fermentation.

In some embodiments, the cross-linking and fermentation steps as described herein are performed in any order. For example, in some embodiments, cross-linking of the food occurs before fermentation of the food. In other embodiments, fermentation is performed before cross-linking. In still other embodiments, the cross-linking and fermentation steps described herein are performed simultaneously. Typically, the present food is subjected to cross-linking prior to fermentation.

It is to be understood that the term "modified food" refers to food after incubation with crosslinking enzymes and after fermentation with microorganisms. In some embodiments, the texture and/or pH of the food may change after the modification steps described herein. For example, before incubation and fermentation the food may be a milk, such as a whole milk, but after incubation and fermentation the modified food, in some embodiments, may be formed into, for example, yogurt, sour milk, acidophilus milk or cheese.

As used herein, the terms "unmodified" in reference to food' or "control" in reference to food means a food, which has not undergone the incubation with cross-linking enzymes and the microbial fermentation described herein. For example, when a food is modified by first cross-linking the food with a cross-linking enzyme and then subjecting the food to fermentation, an unmodified food encompasses those foods, which have not undergone both of these steps in the specified order.

Immunoreactivity

In some embodiments, the level, for example, the presence or amount of immunoreactivity of the modified food may be determined. In various embodiments, the level of immunoreactivity of the modified food may be compared to the level of immunoreactivity in an unmodified food.

As used herein, "immunoreactivity" refers to the ability of an antibody to recognize a native protein or a hydrolyzed cross-linked protein of a food. The term "antibody" (also known as an immunoglobulin) as used herein refers to a large Y-shaped protein produced by plasma cells that is used by the immune system to identify foreign proteins, for example. The antibody recognizes a unique part of the foreign target, e.g., a food allergen (antigen). Each tip of the "Y" of an antibody contains a paratope (a structure analogous to a lock) that is specific for one particular epitope (similarly analogous to a key) on an antigen, allowing these two structures to bind together with precision.

The antibody of the present disclosure may belong to any isotype or class. Accordingly, the antibodies used with the methods of the present disclosure may be IgA, IgA, IgD, IgF, IgG, or IgM antibodies. Typically, the antibody is an IgG or IgE antibody.

In some embodiments, the antibody which is used to determine a level of immunoreactivity in the modified food is a polyclonal antibody. As used herein, the phrase "polyclonal antibody" refers to a composition comprising different antibody molecules which are capable of binding to or reacting with several different specific antigenic determinants (also referred to herein as "epitopes") on the same or on different antigens. The variability in antigen specificity of a polyclonal antibody is located in the variable regions of the individual antibody molecules constituting the polyclonal antibody and in the particular mixture of antibody molecules that constitute the polyclonal antibody.

Typically, a polyclonal antibody useful for assessing the presence or amount of an allergen in a food are prepared using well-known methods, for example, by immunization of an animal with the target antigen or portions thereof and are derived from the blood, milk or colostrum obtained from the immunized animal. For example, a mammal, such as a rabbit, may be injected with a food protein, such as β-casein. This induces the B-lymphocytes to produce IgG immunoglobulins specific for the β-casein. The polyclonal IgG is then purified from the mammal's serum.

In other embodiments, IgE antibodies from the serum of a food-allergy individual or animal may be used against the modified and unmodified foods of the present disclosure to assess the level of immunoreactivity of a modified and/or unmodified food.

In some embodiments, the antibody that is used to detect the hydrolyzed cross-linked protein in a modified food or unmodified food as described herein is a monoclonal antibody. The term "monoclonal antibody" as used herein refers to a preparation of antibodies of a single molecular composition. A monoclonal antibody composition displays a single binding specificity and affinity for a particular epitope of a target antigen. Methods for preparing monoclonal antibodies are well known in the art. See, for example, Harlow and Lane (ed), *Antibodies: A Laboratory Approach*, Cold Spring Harbor Laboratory, New York (1988), which is herein incorporated by reference in its entirety.

In some embodiments, the level of immunoreactivity of a modified food of the disclosure may be determined using an art known immunological assay. Typically, an Enzyme-Linked Immunosorbent Assay (ELISA) is used. ELISA procedures, for example, direct, indirect, competitive and non-competitive ELISAs are well known in the art and can readily be adapted to test for the presence or amount of antigen present in the modified foods of the present disclosure.

For example to detect immunoreactivity of a modified food, an antibody, which binds to a protein in the modified food, such as casein, is bound to a solid phase, e.g., a polystyrene multiwell, plate. The modified food is then added to the solid phase. An unmodified food may also be bound to the solid phase as a control. Following a brief period of incubation, the solid phase is rinsed. The antibody that specifically binds the protein in the unmodified food and/or the cross-linked protein in the modified food can be either directly detected or indirectly detected by way of a labeled secondary antibody, which binds to a protein-binding antibody. Unbound labeled secondary antibody is washed away.

Any appropriate label which may be directly or indirectly visualized may be utilized in these detection assays including, without limitation, an enzyme (e.g., peroxidase, alkali phosphatase and beta-galactosidase), fluorescent substances (e.g., fluorescent isothiocyanate), biologically-luminescent substances (e.g., luciferin-luciferase), chemically luminescent substances (e.g., luminol, an acridine derivative and an adamantane derivative), biotin, avidin, a gold colloid, radioactive materials (e.g., $^{32}P$) etc.

In some embodiments, the label intensity is inversely proportional with the amount of protein present in the modified or unmodified food such as when using a competitive ELISA. In other embodiments, the label intensity reflects the amount of protein present in the modified or unmodified food. For example, in some embodiments, if there are no protein specific immunocomplexes present in the modified food, then substantially no label will be immobilized on the solid phase and will be washed away.

As used herein, "substantially no" refers to almost no detectable antigen specific immunocomplex relative to an amount of strongly detectable antigen specific immunocomplex. For example, the presence of a "background" level of label development would be considered by the skilled artisan to constitute substantially no antigen specific immunocomplex present in the biological sample. Additionally, the amount of immobilized label associated with detectable antigen specific immunocomplex will be about 10 times, typically about 100 times or more typically about 1000 times more intense than the amount of immobilized label associated with "substantially no" immunocomplex.

ELISA kits for detecting food allergens, such as casein, are commercially available from, for example, Astorilab, Poncarale, Italy and Neogen Corporation, Lansing, Mich.

Exemplary immunoassays that may be used with the methods of the present disclosure are described, e.g., in Harlow and Lane (ed), *Antibodies: A Laboratory Approach*, Cold Spring Harbor Laboratory, New York (1988), and Moynagh and Schimmel, Nature 400:105, 1999, which are herein incorporated by reference in their entireties.

In some embodiments, a level of immunoreactivity of the modified food as determined by an ELISA, for example, is less than the level of immunoreactivity of an unmodified food. The phrase "less than" encompasses about 10% less, about 20% less, about 50% less, about 75% less, about 90% less or about 100% less than the amount of immunoreactivity in an unmodified food as determined by, for example, label intensity as described herein.

In some embodiments, the level of immunoreactivity of the modified food is less than the additive effect of reduced immunoreactivity due solely to incubating an unmodified food with a cross-linking enzyme or due solely to fermenting an unmodified food with a microorganism. For instance, as exemplified below, a relative concentration of antigen/antibody complex of 1.0 may be detected using, for example, an ELISA assay in an unmodified food. The relative level of antigen/antibody complex may be reduced to 0.6 by subjecting an unmodified food solely to a cross-linking enzyme and not also to microbial fermentation. The relative level of antigen/antibody complex may be reduced to 0.8 by subjecting an unmodified food solely to microbial fermentation. Accordingly, by combining the two procedures, the relative level of antigen/antibody complex may be reduced to 0.4, if an additive effect is expected. In some embodiments of the present disclosure, however, an unexpected synergistic effect is observed, e.g., a greater level of reduction of immunoreactivity of the modified foods is observed than would be expected by additive effects alone.

In other embodiments, the level of immunoreactivity of a food, which is first incubated with a cross-linking enzyme and then subsequently subjected to microbial fermentation is less than a level of immunoreactivity of a food simultaneously subjected to fermentation and incubation with a cross-linking enzyme. In some embodiments, the food comprises β-casein.

In some embodiments, the present disclosure is directed to modified foods comprising hydrolyzed cross-linked protein, wherein a level of immunoreactivity of an antibody against the modified food is less than a level of immunoreactivity of the antibody against an unmodified food. The modified foods are prepared according to the methods described herein. Foods that are suitable for modification include those that comprise at least one protein. Such foods as described herein include, e.g., milk, eggs, fish, shellfish, peanuts, tree nuts, soy, wheat, corn, beef, chicken and lamb. The variant levels of immunoreactivity of the modified food and the mass distribution of hydrolyzed protein are the same as described above for the methods of the disclosure.

EXAMPLES

Example 1

Transglutaminase Treated β Casein

Purified β casein derived from milk was incubated with commercially available transglutaminase obtained from guinea pig liver (Sigma-Aldrich, St. Louis, Mo., Product No. T 5398) for two hours at 4° C. The reaction mixture was prepared as follows.

1) 100 μl 1 M Tris Acetate, pH 6.0

2) 50 μl 30 μg/ml β casein (derived from milk)

3) 10 μl 2 U/ml transglutaminase from guinea pig liver (Sigma-Aldrich, St. Louis, Mo.)

4) 327.5 μl water 5) 2.5 μl of 1 M $CaCl_2$ (added last)

Three distinct levels of purified β casein (low, medium and high) were also prepared and incubated with 0.08-00125 units of the transglutaminase. All transglutaminase-treated β casein samples were assayed using a double antibody sandwich ELISA for *bovine* casein detection according to the kit manufacturer's instructions (MyBioSource.com, Catalog #MBS564001).

Figure 1:
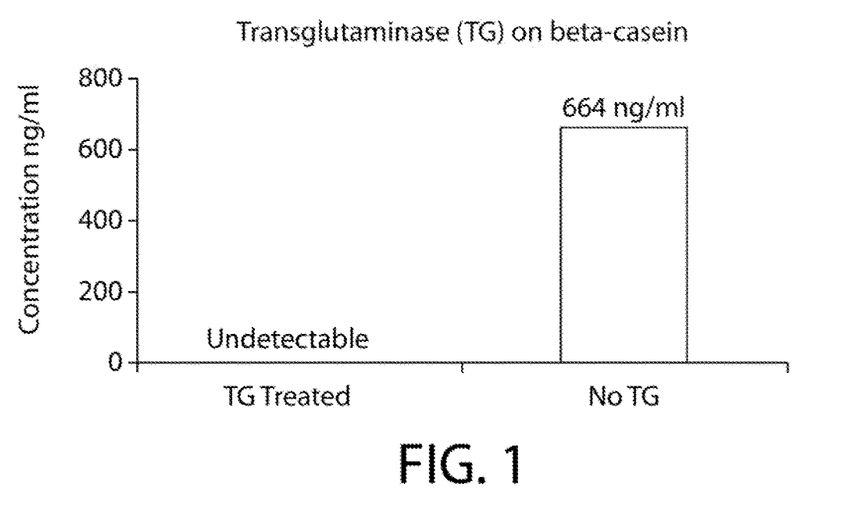

FIG. 1 demonstrates that the purified transglutaminase enzyme was capable of decreasing the immunoreactivity of purified milk-derived β-casein protein. As shown in Table 1, the relative mean amount of β-casein detected was 1. However, upon addition of transglutaminase, the relative mean amount of casein detected was only $5.0 \times 10^{-8}$.

TABLE 1

| CONDITION | MEAN RELATIVE β-CASEIN DETECTED |
| --- | --- |
| Transglutaminase and β-casein | $5.0 \times 10^{-8}$ |
| β-casein | 1 |
| Transglutaminase and 2% milk | 0.15 |
| 2% milk | 1 |

Figure 2:
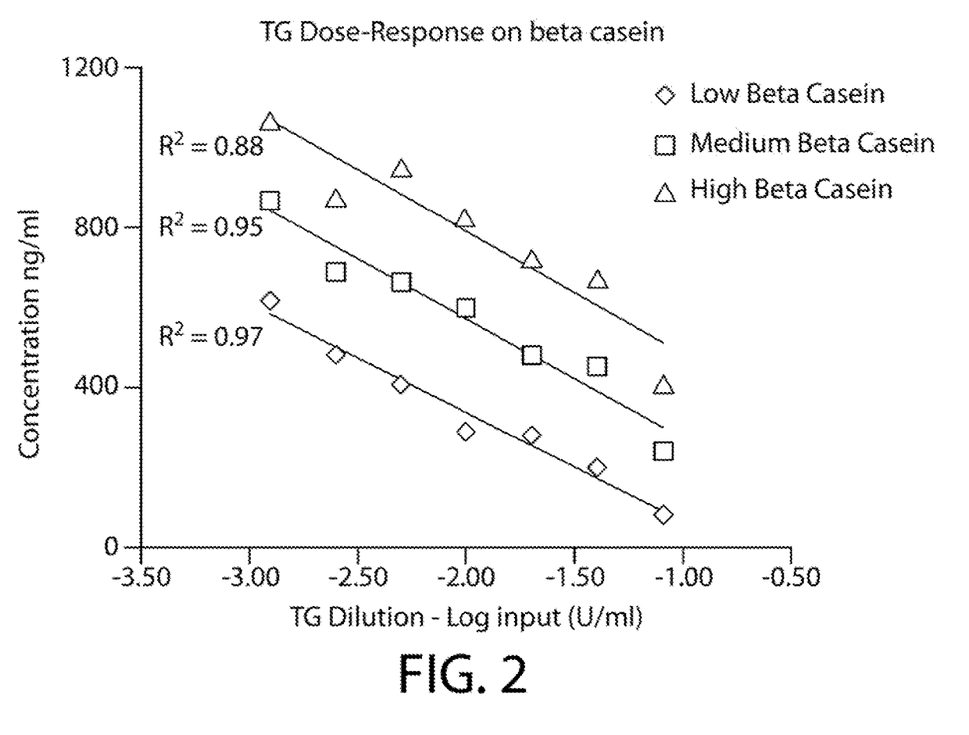

FIG. 2 shows the transglutaminase dose dependent reduction in ELISA immunoreactivity of purified β-casein at the three distinct levels of β-casein. As evidenced in Table 2, increasing the amount of transglutaminase results in a reduction of immunoreactivity for all three levels of casein.

TABLE 2

| | | CASEIN DETECTED | | |
| --- | --- | --- | --- | --- |
| Transglutaminase (U) | Dilution log | Low β-casein Conditions | Medium β-casein Condition | High β-casein Condition |
| 0.08 | −1.10 | 85.44 | 245.67 | 414.44 |
| 0.04 | −1.40 | 200.22 | 456.44 | 675.11 |
| 0.02 | −1.70 | 284.11 | 483.22 | 724.67 |
| 0.01 | −2.00 | 292.56 | 600.89 | 828.67 |
| 0.005 | −2.30 | 409.89 | 666.44 | 953.11 |
| 0.0025 | −2.60 | 484.00 | 689.89 | 878.33 |
| 0.00125 | −2.90 | 617.78 | 868.78 | 1068.00 |

Example 2

Transglutaminase Treated Milk

2% milk samples were also prepared as described in Example 1, above, except that 50 μl of 2% milk diluted to 1000× with phosphate buffered saline 0.01 mol/L PBS (PH=7.0-7.2) replaced the purified β-casein as a substrate for the transglutaminase. The solution was incubated for 24 hours at 4° C. The transglutaminase treated 2% milk was also assayed by the double antibody sandwich ELISA described above.

Figure 3:
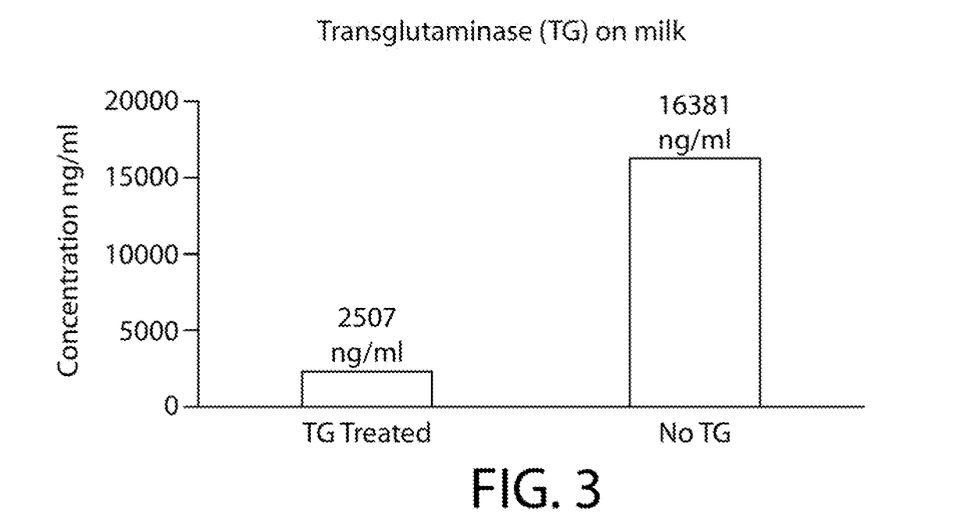

FIG. 3 shows that the transglutaminase reaction is also effective in the intact 2% milk food matrix, which contains fat, carbohydrate, minerals and vitamins as well as proteins in addition to casein (e.g. β-lactoglobulin, α-lactoglobulin, *bovine* serum albumin). As shown in Table 1, above, even in the presence of the food matrix, transglutaminase was able to reduce the level of immunoreactivity of the casein by 85% (mean relative casein level of 1 in the absence of transglutaminase, 0.15 in the presence of transglutaminase).

Example 3

Transglutaminase and Microbial Fermentation

A third trial was carried out by first reacting 2% milk with transglutaminase MooGloo® TI (Modernist Pantry) for 24 hours at 4° C. in an orbital shaker followed by microbial fermentation for 48 hours at 22° C. 900 μl 2% milk were combined with 40 mg MooGloo® TI, which is a mixture of transglutaminase and maltodextrin.

100 μl of a starter culture (2.5 g of starter culture in 10 ml of distilled water) containing *Leuconostoc mesenteroides, Lactobacillus plantarum* and *Pediococcus acidilactici* (Caldwell, Quebec City, Canada) was added to the reaction mixture described above. The fermentation mixture was incubated for 48 hours at 22° C. in an orbital shaker. After fermentation, casein was assayed using a competitive ELISA (Casein ELISA Kit, Astoria, Poncarale, Italy).

Figure 4:
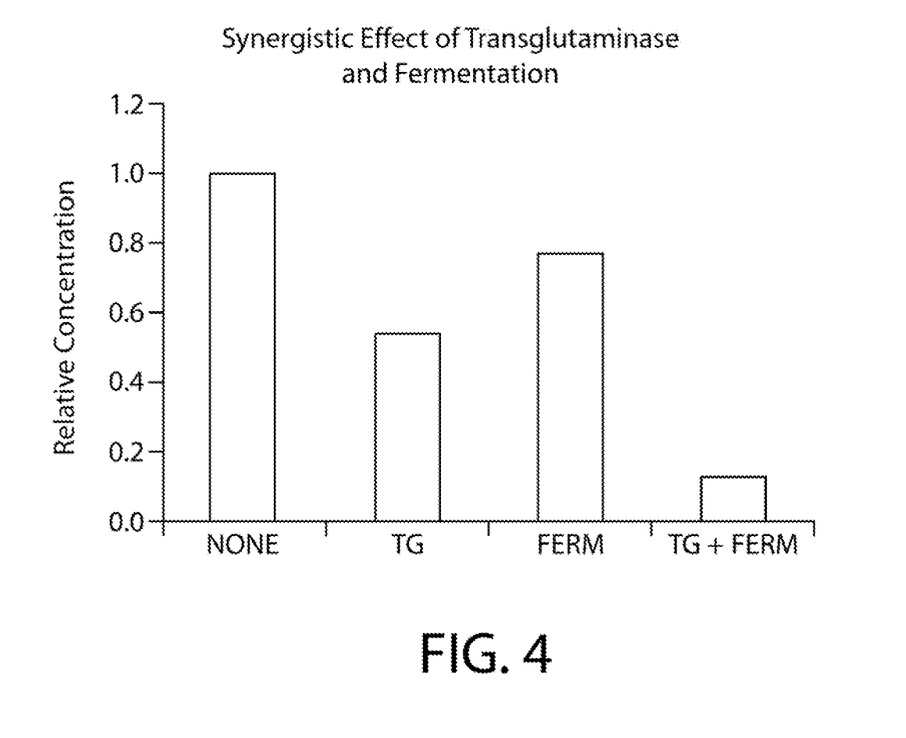

FIG. 4 and Table 3 show that the addition of microbial fermentation to the transglutaminase treatment of milk decreases milk immunoreactivity in the ELISA in a synergistic matter; i.e., the combination of both transglutaminase and fermentation together decrease the immunoreactivity of milk to a greater extent than the sum of the individual effects of these processes when not used in combination. Statistical analysis of the data in FIG. 4 using a generalized linear model and least squared means indicates that all pairwise comparisons are statistically significant. Moreover, there is an interactive effect of transglutaminase treatment and microbial fermentation ($p \leq 0.05$).

TABLE 3

| CONDITION | MEAN RELATIVE CASEIN DETECTED |
|---|---|
| NONE | 1.00 |
| TRANGLUTAMINASE | 0.54 |
| FERMENTATION | 0.77 |
| TRANSGLUTAMINASE AND FERMENTATION | 0.13 |

What is claimed is:

1. A method for reducing immunoreactivity of a food, the method consisting of:
   (a) incubating a food comprising at least one protein with a cross-linking enzyme to form a food comprising at least one cross-linked protein; and
   (b) fermenting the food comprising the at least one cross-linked protein with a microorganism to form a modified food comprising a hydrolysate of the at least one cross-linked protein,
   wherein fermenting the food comprises hydrolyzing the at least one cross-linked protein,
   wherein (a) is performed before (b),
   wherein the microorganism consists of a combination of *Leuconostoc mesenteroides, Lactobacillus plantarum*, and *Pediococcus acidilactici*,
   wherein the food is selected from the group consisting of milk, eggs, fish, shellfish, peanuts, tress nuts, wheat, corn, beef, chicken, and lamb,
   wherein the level of immunoreactivity of the modified food is less than a level of immunoreactivity of a food simultaneously fermented with a microorganism and incubated with a cross-linking enzyme,
   wherein the microorganism is alive during fermentation of the food, and
   wherein a level of immunoreactivity of the modified food is less than a level of immunoreactivity of an unmodified food comprising the at least one protein.

2. The method of claim 1, wherein the at least one protein is selected from the group consisting of gliadin, Gly m Bd 30K, iso Ara h3, parvalbumin, tropomyosin and arginine kinase (40 kDa).

3. The method of claim 1, wherein the cross-linking enzyme is transglutaminase.

4. The method of claim 1, wherein the food comprising at least one protein is milk.

5. The method of claim 4, wherein the milk is cow's milk.

6. The method of claim 1, wherein the at least one protein is β-casein.

7. The method of claim 1, wherein the fermenting comprises:
   hydrolyzing at a temperature of about 22° C.

8. The method of claim 1, wherein the food is nutritionally incomplete.

9. The method of claim 1, wherein the food is a complete and nutritionally-balanced food.

10. The method of claim 1, wherein the cross-linking enzyme is tyrosinase.

11. The method of claim 1, wherein the cross-linking enzyme consists of tyrosinase and transglutaminase.

12. A method for reducing immunoreactivity of a food, the method consisting of:
   incubating a food comprising at least one protein with a cross-linking enzyme to form a food comprising at least one cross-linked protein for a time period of 0.5 hours to 48 hours at a temperature of 2° C. to 5° C., wherein the cross-linking enzyme is transglutaminase;
   inactivating the cross-linking enzymes by heating for at least 3 minutes at 90° C. or higher; and
   fermenting the food comprising the at least one cross-linked protein with a microorganism to form a modified food comprising a hydrolysate of the at least one cross-linked protein for a time period of 2 hours to 4 days at a temperature of 20° C. to 48° C.,
   wherein the microorganism is alive during fermentation of the food,
   wherein the food comprising the at least one protein is milk,
   wherein the microorganism consists of a combination of *Leuconostoc mesenteroides, Lactobacillus plantarum*, and *Pediococcus acidilactici*,
   wherein a level of immunoreactivity of the modified food is less than a level of immunoreactivity of an unmodified food comprising the at least one protein; and
   wherein the level of immunoreactivity of the modified food is less than a level of immunoreactivity of a food simultaneously fermented with a microorganism and incubated with a cross-linking enzyme.

13. The method of claim 12, wherein the food is incubated for a time period of about 24 hours at a temperature of about 4° C.

14. The method of claim 13, wherein the food comprising the at least one cross-linked protein is fermented for a time period of about 48 hours at a temperature of about 22° C.

15. The method of claim 14, wherein the cross-linking enzyme is inactivated after incubation.

16. A method for reducing immunoreactivity of a food, the method consisting of:
   (a) incubating a food comprising at least one protein with a cross-linking enzyme to form a food comprising at least one cross-linked protein; and
   (b) fermenting the food comprising the at least one cross-linked protein with a microorganism to form a modified food comprising a hydrolysate of the at least one cross-linked protein,
   wherein fermenting the food comprises hydrolyzing the at least one cross-linked protein,
   wherein (a) is performed before (b),
   wherein the microorganism consists of a fungus and a combination of *Leuconostoc mesenteroides, Lactobacillus plantarum*, and *Pediococcus acidilactici*,
   wherein the food is selected from the group consisting of milk, eggs, fish, shellfish, peanuts, tress nuts, wheat, corn, beef, chicken, and lamb,
   wherein the level of immunoreactivity of the modified food is less than a level of immunoreactivity of a food simultaneously fermented with a microorganism and incubated with a cross-linking enzyme,
   wherein the microorganism is alive during fermentation of the food, and
   wherein a level of immunoreactivity of the modified food is less than a level of immunoreactivity of an unmodified food comprising the at least one protein.

17. The method of claim 16, wherein the fungus is selected from the group consisting of *Saccharomyces, Aspergillus, Rhizopus, Mucor*, and a combination thereof.

18. The method of claim 17, wherein the fungus consists of *Aspergillus*.

* * * * *